(12) United States Patent  
Yoshioka

(10) Patent No.: US 9,347,353 B2  
(45) Date of Patent: May 24, 2016

(54) ABNORMALITY DETECTION APPARATUS FOR ELECTRICALLY HEATED CATALYST

(75) Inventor: Mamoru Yoshioka, Susono (JP)

(73) Assignee: TOYOTA JIDOSHA KABUSHIKI KAISHA, Toyota-shi (JP)

( * ) Notice: Subject to any disclaimer, the term of this patent is extended or adjusted under 35 U.S.C. 154(b) by 193 days.

(21) Appl. No.: 14/367,551

(22) PCT Filed: Dec. 21, 2011

(86) PCT No.: PCT/JP2011/079707  
§ 371 (c)(1),  
(2), (4) Date: Jun. 20, 2014

(87) PCT Pub. No.: WO2013/094039  
PCT Pub. Date: Jun. 27, 2013

(65) Prior Publication Data  
US 2015/0285117 A1 Oct. 8, 2015

(51) Int. Cl.  
*F01N 3/20* (2006.01)  
*F01N 11/00* (2006.01)  
(Continued)

(52) U.S. Cl.  
CPC ............ *F01N 3/2013* (2013.01); *F01N 3/2006* (2013.01); *F01N 3/2026* (2013.01); *F01N 3/2853* (2013.01); *F01N 3/2864* (2013.01); *F01N 11/00* (2013.01); *G01N 27/14* (2013.01); *F01N 2550/22* (2013.01); *F01N 2900/0602* (2013.01); *F01N 2900/1404* (2013.01); *Y02T 10/26* (2013.01); *Y02T 10/47* (2013.01)

(58) Field of Classification Search  
USPC ....................................................... 73/114.75  
See application file for complete search history.

(56) References Cited

U.S. PATENT DOCUMENTS 7,284,365 B2 * 10/2007 Abe ...................... F01N 3/2013  
                                                            60/277  
8,091,663 B2 * 1/2012 Ichikawa ............... B60K 6/445  
                                                   180/65.265  
(Continued)

FOREIGN PATENT DOCUMENTS

| JP | 2002 21541 | 1/2002 |
|---|---|---|
| JP | 2005 9364 | 1/2005 |
| JP | 2009 274471 | 11/2009 |

OTHER PUBLICATIONS

International Search Report Issued Mar. 19, 2012 in PCT/JP11/079707 Filed Dec. 21, 2011.

*Primary Examiner* — Freddie Kirkland, III  
(74) *Attorney, Agent, or Firm* — Oblon, McClelland, Maier & Neustadt, L.L.P

(57) ABSTRACT

Abnormality of an electrically heated catalyst is detected in a more accurate manner. In an abnormality detection apparatus for an electrically heated catalyst which is provided with a heat generation element that is arranged in an exhaust passage of an internal combustion engine, and is electrically energized to generate heat, and an insulation part that provides electrical insulation so that electricity does not flow through the exhaust passage when the heat generation element is electrically energized, provision is made for a determination unit which makes a determination that abnormality has occurred in the electrically heating catalyst, in cases where the heat generation element is electrically energized from before starting of the internal combustion engine, and in cases where a value of an insulation resistance of the insulation part after a predetermined period of time has elapsed from the starting of the internal combustion engine is equal to or less than a threshold value.

5 Claims, 10 Drawing Sheets

(51) Int. Cl.
  *F01N 3/28*    (2006.01)
  *G01N 27/14*   (2006.01)

(56) References Cited

U.S. PATENT DOCUMENTS

| | | | | |
|---|---|---|---|---|
| 8,423,221 B2* | 4/2013 | Watanabe | ............. | F01N 3/2026 701/22 |
| 8,661,796 B2* | 3/2014 | Yoshioka | ............. | F01N 3/2013 60/295 |
| 8,826,643 B2* | 9/2014 | Yoshioka | ............. | F01N 3/2013 60/277 |
| 9,206,728 B2* | 12/2015 | Tanaka | ................... | F01N 11/00 |
| 2005/0022509 A1 | 2/2005 | Fukusako et al. | | |
| 2009/0277705 A1 | 11/2009 | Ichikawa | | |
| 2012/0004801 A1* | 1/2012 | Watanabe | ............. | F01N 3/2026 701/22 |
| 2012/0247090 A1* | 10/2012 | Yoshioka | ............. | F01N 3/2013 60/286 |
| 2012/0260638 A1* | 10/2012 | Yoshioka | ............. | F01N 3/2013 60/295 |

* cited by examiner

ABNORMALITY DETECTION APPARATUS FOR ELECTRICALLY HEATED CATALYST

TECHNICAL FIELD

The present invention relates to an abnormality detection apparatus for an electrically heated catalyst.

BACKGROUND ART

As an exhaust gas purification catalyst arranged in an exhaust passage of an internal combustion engine, there has been developed an electrically heated catalyst (hereinafter, may also be referred to as an EHC) in which a catalyst is heated by means of a heat generation element which generates heat by electrical energization thereof.

Here, there is known a technology in which in a hybrid vehicle, electric resistance is detected at the time of electrical energization of an electrically heated catalyst, so that an abnormality in the electrically heated catalyst is determined based on the electric resistance thus detected (for example, refer to a first patent literature).

In addition, there is also known a technology of estimating the temperature of a mat which serves to support a catalyst (for example, refer to a second patent literature).

Moreover, there is also known a technology in which leakage of electricity or short circuit is determined based on an electric current, a voltage or the like at the time when a high voltage is applied to discharge electrodes, and when a short circuit occurs, the supply of electric power is limited (for example, refer to a third patent literature).

However, when an internal combustion engine is started in a state where the temperature of an electrically heated catalyst is not high enough, water or moisture may condense in an electrically heated catalyst. A value of an insulation resistance between the electrically heated catalyst and an exhaust passage is changed due to this condensed water. In the past, a change in the value of the insulation resistance due to the condensed water is not taken into consideration, so there is a fear that accuracy in detecting an abnormality may become low.

PRIOR ART REFERENCES

Patent Literatures

[First Patent Literature] Japanese Patent Laid-Open Publication No. 2009-274471
[Second Patent Literature] Japanese Patent Laid-Open Publication No. 2005-009364
[Third Patent Literature] Japanese Patent Laid-Open Publication No. 2002-021541

SUMMARY OF THE INVENTION

Problems to be Solved by the Invention

The present invention has been made in view of the above-mentioned problem, and has for its object to detect an abnormality in an electrically heated catalyst in a more accurate manner.

Means for Solving the Problems

In order to achieve the above-mentioned problem, an abnormality detection apparatus for an electrically heated catalyst according to the present invention includes:

a heat generation element that is arranged in an exhaust passage of an internal combustion engine, and generates heat by electrical energization thereof; and an insulation part that provides electrical insulation so as to prevent electricity from flowing through said exhaust passage when said heat generation element is electrically energized;

wherein provision is made for a determination unit which makes a determination that abnormality has occurred in said electrically heating catalyst, in cases where said heat generation element is electrically energized from before starting of said internal combustion engine, and in cases where a value of an insulation resistance of said insulation part after a predetermined period of time has elapsed from the starting of said internal combustion engine is equal to or less than a threshold value.

The heat generation element may also be a carrier for the catalyst, or may also be arranged at the upstream side of the catalyst. By electrically energizing the heat generation element, the heat generation element generates heat, so that the temperature of the catalyst can be caused to rise. The insulation part is provided so as to prevent electricity or electric current from flowing. However, if condensed water attaches or adheres to the insulation part, electricity may flow thereto through the condensed water. That is, the value of the insulation resistance of the insulation part is decreased due to the condensed water.

Here, if the electrically heated catalyst is normal, the temperature of the electrically heated catalyst can be made sufficiently high by the time the internal combustion engine is started, by electrically energizing the heat generation element from before the starting of the internal combustion engine. For this reason, it becomes difficult for condensed water to be generated, thus making it possible to suppress the value of the insulation resistance of the insulation part from decreasing.

On the other hand, when an abnormality occurs in the electrically heated catalyst, even if the heat generation element is intended to be electrically energized from before the starting of the internal combustion engine, the temperature of the electrically heated catalyst will not go up. For this reason, it becomes easy for condensed water to be generated at the time of the starting of the internal combustion engine, so the value of the insulation resistance of the insulation part decreases. That is, the value of the insulation resistance after the predetermined period of time has elapsed from the starting of the internal combustion engine becomes equal to or less than the threshold value.

This threshold value can be made to be an upper limit value of the insulation resistance during the time when condensed water is generated. In addition, the threshold value may also be set to a value smaller than the value of the insulation resistance which is within an allowable range. Moreover, the predetermined period of time can also be made to be a period of time in which when an abnormality occurs in the electrically heated catalyst, condensed water is generated, whereas when the electrically heated catalyst is normal, condensed water is not generated. Here, note that the determination unit may make a comparison between the value of the insulation resistance at an arbitrary point in time during this predetermined period of time and the threshold value, or may make a comparison between an average value or a minimum value of the insulation resistance during this predetermined period of time and the threshold value.

In this manner, if an abnormality occurs in the electrically heated catalyst, condensed water will be generated after the starting of the internal combustion engine. Then, there is a correlation between the value of the insulation resistance after the lapse of the predetermined period of time from the starting of the internal combustion engine, and the generation of condensed water. Accordingly, the determination unit can determine based on this correlation whether an abnormality occurs in the electrically heated catalyst.

Here, note that the abnormality of the electrically heated catalyst referred to herein means a case in which the temperature of the electrically heated catalyst does not rise, or a case in which a temperature rise of the electrically heated catalyst is insufficient with respect to the electric energy supplied. This may also be considered to be a break in an electric wire for supplying electric power to the heat generation element, or damage to the electrically heated catalyst, or a failure of a control device, for example. In addition, this may also be an abnormality in which the heat generation element can not be electrically energized.

Moreover, in the present invention, said determination unit can make said threshold value larger in accordance with the increasing temperature of said internal combustion engine at the time of the starting of said internal combustion engine.

Here, it is considered that the higher the temperature of the internal combustion engine at the time of the starting thereof, the higher the temperature of the exhaust passage or the electrically heated catalyst is, too. Then, the higher the temperature of the exhaust passage or the electrically heated catalyst, the more difficult it becomes for condensed water to be generated. On the other hand, the lower the temperature of the internal combustion engine, the larger the amount of generation of the condensed water becomes. Thus, the higher the temperature of the internal combustion engine at the time of the starting thereof, the more difficult it becomes for condensed water to be generated, and hence, the more difficult it becomes for the value of the insulation resistance to decrease. Accordingly, by correcting the threshold value according to the temperature of the internal combustion engine, the accuracy in the abnormality determination of the electrically heated catalyst can be enhanced.

Here, note that the temperature of the internal combustion engine at the time of the starting of the internal combustion engine may also be as the temperature of the internal combustion engine, or the temperature of cooling water in the internal combustion engine, or the temperature of lubricating oil in the internal combustion engine at the point in time at which the starting of the internal combustion engine is commenced. In addition, this may also include the temperature of the internal combustion engine immediately before or immediately after the starting of the internal combustion engine, which is substantially the same as the temperature of the internal combustion engine at the time of the starting of the internal combustion engine. Moreover, instead of changing the threshold value, the value of the insulation resistance may be corrected.

In addition, in the present invention, said determination unit can make said threshold value larger in accordance with the increasing value of said insulation resistance at the time of the starting of said internal combustion engine.

Here, the value of the insulation resistance may already be low at the time of the starting of the internal combustion engine. For example, when particulate matter (hereinafter also referred to as PM) in an exhaust gas has attached or adhered to the electrically heated catalyst at the time of the last operation of the internal combustion engine, the value of the insulation resistance will decrease. In such a case, when condensed water has been generated after the starting of the internal combustion engine, the value of the insulation resistance becomes smaller. Accordingly, by correcting said threshold value according to the value of the insulation resistance at the time of the starting of the internal combustion engine, the accuracy in the abnormality determination of the electrically heated catalyst can be enhanced.

Here, note that in place of the value of the insulation resistance at the time of the starting of the internal combustion engine, there may also be used the value of the insulation resistance before the starting of the internal combustion engine, the value of the insulation resistance before electrical energization of the electrically heated catalyst, or the value of the insulation resistance at the point in time at which electrical energization to the electrically heated catalyst has been started. In addition, instead of changing the threshold value, the value of the insulation resistance may be corrected.

Moreover, in the present invention, said determination unit can make said threshold value larger in accordance with the increasing electric energy which has been supplied to said heat generation element by the time said internal combustion engine is started.

Here, even if the heat generation element has been electrically energized before the starting of the internal combustion engine, when the electric energy supplied is small, the temperature of the heat generation element may not go up to a sufficient extent. For example, in cases where a period of time in which electric power has been supplied is short, or in cases where a voltage or electric current is small, the electric energy becomes small. Then, when the electrically heated catalyst is normal, the temperature of the heat generation element becomes higher as the electric energy supplied to the heat generation element is larger, so it becomes difficult for condensed water to be generated. Accordingly, by correcting said threshold value according to the electric energy supplied to the heat generation element by the time the internal combustion engine is started, the accuracy in the abnormality determination of the electrically heated catalyst can be enhanced. Here, note that instead of changing the threshold value, the value of the insulation resistance may be corrected.

Further, in the present invention, said determination unit can make a determination that abnormality has occurred in said electrically heating catalyst, in cases where said heat generation element is electrically energized from before the starting of said internal combustion engine until after the starting of said internal combustion engine, and in cases where the value of the insulation resistance of said insulation part after the predetermined period of time has elapsed from the starting of said internal combustion engine is equal to or less than a threshold value.

Here, in cases where the time of energization to the heat generation element before the starting of the internal combustion engine is short, and in cases where the temperature of the electrically heated catalyst is not high enough at the time of the starting of the internal combustion engine, there will be a fear that condensed water may be generated after the starting of the internal combustion engine. Even in such a case, when the electrically heated catalyst is normal, the condensed water can be quickly removed by continuing the electrical energization to the heat generation element after the starting of the internal combustion engine. In that case, the value of the insulation resistance lowered after the starting of the internal combustion engine quickly becomes large after that. On the other hand, if an abnormality occurs in the electrically heated catalyst, it will take time for the condensed water to be removed after the starting of the internal combustion engine. Accordingly, in cases where the heat generation element has been electrically energized until after the starting of said internal combustion engine, and if the value of the insulation resistance after the lapse of the predetermined period of time from the starting of the internal combustion engine is equal to or less than the threshold value, a determination can be made that an abnormality has occurred in the electrically heating catalyst.

Effect of the Invention

According to the present invention, the abnormality of the electrically heated catalyst can be detected in a more accurate manner.

MODES FOR CARRYING OUT THE INVENTION

Hereinafter, specific embodiments of the present invention will be described based on the attached drawings. However, the dimensions, materials, shapes, relative arrangements and so on of component parts described in the embodiments are not intended to limit the technical scope of the present invention to these alone in particular as long as there are no specific statements.

First Embodiment

Figure 1:
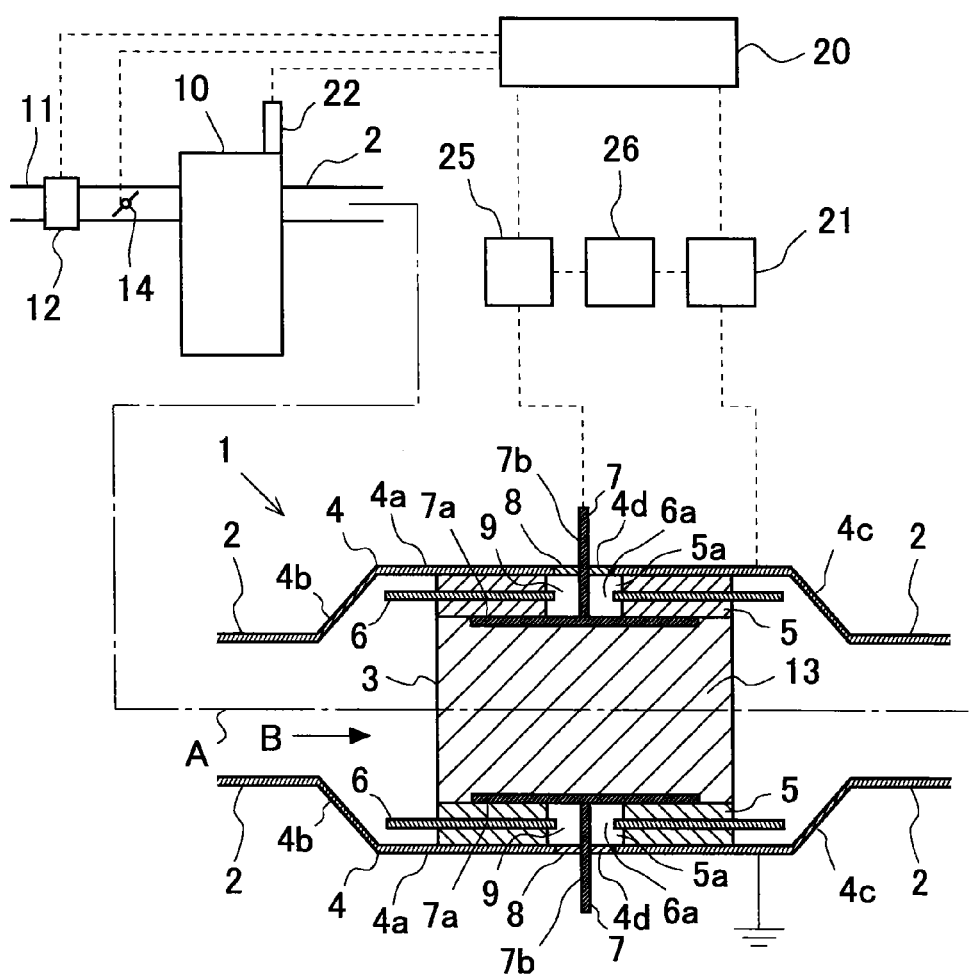
FIG. 1 is a view showing the schematic construction of an electrically heated catalyst according to embodiments of the present invention.

FIG. 1 is a view showing the schematic construction of an electrically heated catalyst 1 according to embodiments of the present invention. An electrically heated catalyst 1 (hereinafter, referred to as an EHC 1) according to the embodiments is arranged in an exhaust pipe 2 of an internal combustion engine 10. The internal combustion engine 10 is a gasoline engine for driving a vehicle. However, the internal combustion engine is not limited to the gasoline engine, but may be a diesel engine, etc. In addition, the internal combustion engine 10 may be mounted on a hybrid vehicle which is provided with an electric motor. Here, note that an arrow B in FIG. 1 indicates the direction of the flow of an exhaust gas in the exhaust pipe 2.

On the internal combustion engine 10, there is provided a water temperature sensor 22 for detecting the temperature of cooling water. In addition, an intake pipe 11 is connected to the internal combustion engine 10. An air flow meter 12 for measuring an amount of intake air in the internal combustion engine 10 is arranged in the intake pipe 11 of the internal combustion engine 10. Also, a throttle valve 14 is arranged in the intake pipe 11 at the downstream side of the air flow meter 12.

The EHC 1 is provided with a catalyst carrier 3, a case 4, a mat 5, an inner pipe 6, and electrodes 7. The catalyst carrier 3 is formed in the shape of a circular column, and is arranged in such a manner that a central axis thereof is in alignment with a central axis A of the exhaust pipe 2. A catalyst 13 is carried or supported by the catalyst carrier 3. Here, note that for the catalyst supported on the catalyst carrier 3, there is mentioned by way of example, a three-way catalyst, an oxidation catalyst, an NOx storage reduction catalyst, or an NOx selective reduction catalyst.

The catalyst carrier 3 is formed of a material which, when electrically energized, becomes an electric resistance to generate heat. As a material for the catalyst carrier 3, there can be mentioned SiC by way of example. The catalyst carrier 3 has a plurality of passages which extend in a direction B in which the exhaust gas flows (i.e., the direction of the central axis A), and which have a cross section of honeycomb shape vertical to the direction in which the exhaust gas flows. The exhaust gas flows through these passages. Here, note that the cross sectional shape of the catalyst carrier 3 in a direction orthogonal to the central axis A may also be elliptical, etc. In addition, the central axis A is a common central axis with respect to the exhaust pipe 2, the catalyst carrier 3, the inner pipe 6, and the case 4.

Here, note that in this embodiment, the catalyst carrier 3 corresponds to a heat generation element according to the present invention. However, the heat generation element according to the present invention is not limited to a carrier carrying or supporting a catalyst. For example, the heat generation element may be a structural member which is arranged at the upstream side of a catalyst.

The catalyst carrier 3 is received in the case 4. Electrode chambers 9 are formed inside the case 4. Here, note that the details of the electrode chambers 9 will be described later.

The case 4 is formed of metal. As a material which forms the case 4, there can be mentioned a stainless steel material, by way of example. The case 4 has a receiving portion 4a which is constructed to include a curved surface parallel to the central axis A, and tapered portions 4b, 4c which serve to connect the receiving portion 4a and the exhaust pipe 2 with each other at the upstream side and at the downstream side, respectively, of the receiving portion 4a. The receiving portion 4a has a channel cross section which is larger than that of the exhaust pipe 2, and the catalyst carrier 3, the mat 5 and the inner pipe 6 are received in the inside of the receiving portion 4a. The tapered portions 4b, 4c each take a tapered shape of which the channel cross section decreases in accordance with the increasing distance thereof from the receiving portion 4a. Here, note that the case 4 is grounded electrically.

The mat 5 is inserted between an inner peripheral surface of the receiving portion 4a of the case 4, and an outer peripheral surface of the catalyst carrier 3. In other words, in the inside of the case 4, the catalyst carrier 3 is supported by the mat 5. In addition, the inner pipe 6 is inserted in the mat 5. That is, the mat 5 is divided into a portion at the side of the case 4 and a portion at the side of the catalyst carrier 3 by means of the inner pipe 6. The inner pipe 6 is a tubular member with the central axis A being located as a center thereof.

The mat 5 is formed of an electrically insulating material. As a material which forms the mat 5, there can be mentioned, by way of example, a ceramic fiber which includes alumina as a main component. The mat 5 is wound around the outer peripheral surface of the catalyst carrier 3 and the outer peripheral surface of the inner pipe 6. Due to the insertion of the mat 5 between the catalyst carrier 3 and the case 4, it is possible to suppress electricity from flowing to the case 4 at the time when the catalyst carrier 3 is electrically energized.

The inner pipe 6 is formed of a stainless steel material. In addition, an electrically insulating layer is formed on the entire surface of the inner pipe 6. As a material which forms the electrically insulating layer, ceramic or glass can be mentioned by way of example. Here, note that the inner pipe 6 as a whole may be formed of an electrically insulating material such as alumina or the like. Moreover, as shown in FIG. 1, the inner pipe 6 has a length in the direction of the central axis A longer than that of the mat 5. As a result, the inner pipe 6 has an upstream side end and a downstream side end thereof protruding from an upstream side end face and a downstream side end face of the mat 5, respectively.

A pair of electrodes 7 are connected to the catalyst carrier 3. The electrodes 7 are connected to the outer peripheral surface of the catalyst carrier 3, while passing through the electrode chambers 9, respectively, from the outside of the case 4. Each electrode 7 is formed of a surface electrode 7a and a shaft electrode 7b. Each surface electrode 7a extends along the outer peripheral surface of the catalyst carrier 3 in a circumferential direction and in the axial direction. In addition, the surface electrodes 7a are arranged on the outer peripheral surface of the catalyst carrier 3 in such a manner that they are mutually opposed to each other with the catalyst carrier 3 being sandwiched therebetween. Each shaft electrode 7b has one end thereof connected to a corresponding surface electrode 7a. And, each shaft electrode 7b has the other end thereof protruded to the outside of the case 4 through the corresponding electrode chamber 9.

The case 4, the mat 5 and the inner pipe 6 have through holes 4d, 5a, 6a opened therein so as to allow the shaft electrodes 7b to pass therethrough, respectively. Then, in the case 4, each electrode chamber 9 is formed by a space which is surrounded by the circumferential surface of the corresponding through hole 5a in the mat 5. Here, note that an electrode chamber 9 may be formed over the entire circumference of the outer peripheral surface of the catalyst carrier 3, by dividing the mat 5 into an upstream side portion and a downstream side portion, which are arranged separately from each other with a space therebetween.

Insulation parts 8, which serve to support the shaft electrodes 7b, respectively, are arranged or inserted in the through holes 4d which are opened in the case 4. The insulation parts 8 are each formed of an electrically insulating material, and are fitted with no gap between the case 4 and the electrodes 7.

The shaft electrodes 7b have the other ends thereof electrically connected to a battery 26 through a power control unit 25. Electric power is supplied to the electrodes 7 from the battery 26 through the power control unit 25. When electric power is supplied to the electrodes 7, the catalyst carrier 3 is electrically energized. When the catalyst carrier 3 generates heat by electrical energization thereof, the catalyst 13 supported by the catalyst carrier 3 is heated, so that the activation thereof is facilitated. The power control unit 25 serves to switch on and off the supply of electric power to the electrodes 7 (i.e., energization to the catalyst carrier 3), and to adjust the electric power to be supplied thereto.

In addition, the EHC 1 is provided with a measuring device 21 for measuring a value of an insulation resistance between an electrode 7 and the case 4. It can also be said that this measuring device 21 measures the value of the insulation resistance of an insulation part 8.

Figure 2:
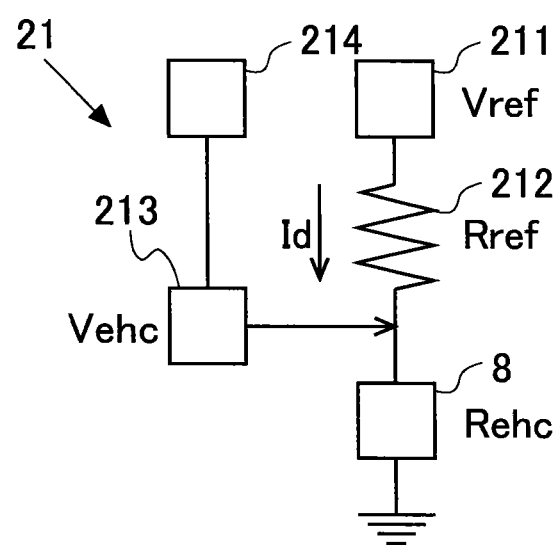
FIG. 2 is a view showing the schematic construction of a measuring device.

FIG. 2 is a view showing the schematic construction of the measuring device 21. The measuring device 21 is provided with a reference power supply 211, a reference resistance 212, a voltmeter 213, and a resistance value calculation circuit 214. As shown in FIG. 2, the reference resistance 212 and the insulation part 8 are connected in series with each other. And, the reference power supply 211 applies a reference voltage, which is an amplified voltage supplied from the battery 26, to the reference resistance 212 and the insulation part 8. The voltmeter 213 measures a voltage at a location between the reference resistance 212 and the insulation part 8 at the time when the reference voltage is applied to the reference resistance 212 and the insulation part 8 from the reference power supply 211. The resistance value calculation circuit 214 calculates the value of the insulation resistance of the insulation part 8 based on the voltage measured by the voltmeter 213.

Here, note that when representing a voltage (reference voltage) of the reference power supply 211 by Vref, a resistance value (a reference resistance value) of the reference resistance 212 by Rref, an electric current flowing through the reference resistance 212 and the insulation part 8 by Id, and the voltage measured by means of the voltmeter 213 by Vehc, the insulation resistance value Rehc of the insulation part 8 is represented by the following equations (1) and (2). The resistance value calculation circuit 214 calculates the insulation resistance value of the insulation part 8 by the use of these equations (1) and (2).

$$Id = (Vref - Vehc)/Rref \qquad (1)$$

$$\begin{aligned} Rehc &= Vehc/Id \\ &= Vehc/((Vref - Vehc)/Rref) \\ &= Vehc/(Vref - Vehc) * Rref \end{aligned} \qquad (2)$$

The power control unit 25 is electrically connected to an electronic control unit (ECU) 20 which is provided in combination with the internal combustion engine 10. In addition, the throttle valve 14 is also electrically connected to the ECU 20. Thus, these parts are controlled by the ECU 20.

In addition, the air flow meter 12, the measuring device 21 and the water temperature sensor 22 are electrically connected to the ECU 20. Thus, output values (signals) of the individual sensors and a measured value of the measuring device 21 are inputted to the ECU 20.

Here, when the temperature of the EHC 1 is not high enough at the time of cold start of the internal combustion engine 10, the temperature of the exhaust gas passing through the electrode chambers 9 is low, and hence, the water contained in the exhaust gas condenses in the electrodes 7 or the insulation parts 8. In that case, the value of the insulation resistance between the electrodes 7 and the case 4, i.e., the value of the insulation resistance of each insulation part 8, will become low. On the other hand, the temperature of the EHC 1 can be made high enough at the time of starting of the internal combustion engine 10 by electrically energizing the catalyst carrier 3 from before the starting of the internal combustion engine 10. As a result of this, it is possible to suppress the value of the insulation resistance from becoming low after the starting of the internal combustion engine 10.

However, in cases where electricity does not flow through the catalyst carrier 3, the value of the insulation resistance becomes low after the starting of the internal combustion engine 10. Accordingly, in this embodiment, in cases where the value of the insulation resistance after the lapse of a predetermined period of time from the starting of the internal combustion engine 10 is equal to or less than a threshold value R2, a determination is made that an abnormality occurs in the EHC 1. On the other hand, in cases where the value of the insulation resistance after the lapse of the predetermined period of time from the starting of the internal combustion engine 10 is larger than the threshold value R2, a determination is made that the EHC 1 is normal.

Figure 3:
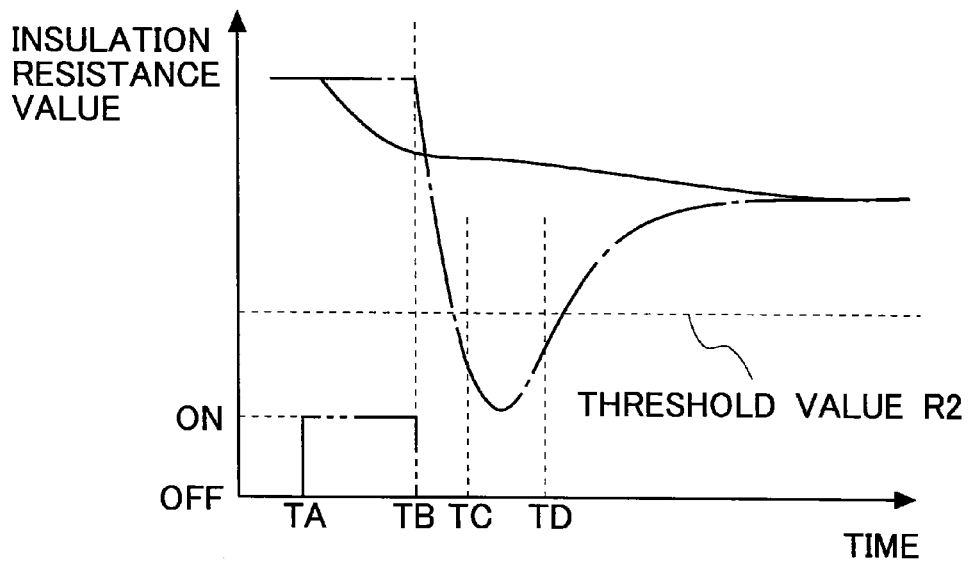
FIG. 3 is a time chart showing the change over time of a value of an insulation resistance before and after starting of an internal combustion engine.

Here, FIG. 3 is a time chart showing the change over time of the value of the insulation resistance before and after the starting of the internal combustion engine 10. A solid line indicates the value of the insulation resistance at the time of normal operation, and an alternate long and short dash line indicates the value of the insulation resistance at the time of abnormal operation. In addition, an alternate long and two short dashes line indicates electric power to be supplied (hereinafter referred to as supply power). When the supply power is on, electric power is supplied to the catalyst carrier 3, whereas when the supply power is off, the supply of electric power to the catalyst carrier 3 is stopped.

In FIG. 3, at a point in time indicated by TA, the supply of electric power to the catalyst carrier 3 is started. At a point in time indicated by TB, the internal combustion engine 10 is started up. Then, in this embodiment, at the point in time TB at which the internal combustion engine 10 is started, the supply of electric power to the catalyst carrier 3 is stopped. That is, electric power is supplied to the catalyst carrier 3 in a period of time from TA to TB. Then, based on the value of the insulation resistance in a period of time from TC to TD after the point in time TB at which the internal combustion engine 10 is started, it is determined whether the EHC 1 is abnormal. The period of time from TC to TD has been obtained in advance through experiments, etc., as a period of time in which the value of the insulation resistance becomes low, in cases where sufficient electric power is not supplied to the catalyst carrier 3. Here, note that, in this embodiment, the period of time from TC to TD is defined in association with an integrated value of an amount of intake air in the internal combustion engine 10. That is, an amount of condensed water generated in the electrode chambers 9 changes according to the integrated value of the amount of intake air in the internal combustion engine 10, and hence, a period of time in which the amount of condensed water is large is defined based on the integrated value of the amount of intake air.

Here, when the EHC 1 is normal, from the point in time TA at which the supply of electric power to the catalyst carrier 3 is started, the value of the insulation resistance will decrease gently or gradually, and will converge as it is. On the other hand, when the EHC 1 is abnormal, from the point in time TB at which the internal combustion engine 10 is started, the value of the insulation resistance will decrease to a large extent, and thereafter will go up and converge.

That is, if the EHC 1 is normal, the temperature thereof will become high to a sufficient extent before the point in time TB at which the internal combustion engine 10 is started. For this reason, after the point in time TB at which the internal combustion engine 10 is started, condensed water will not be generated at all, or even if generated, it will be a small amount. Accordingly, after the point in time TB at which the internal combustion engine 10 is started, the value of the insulation resistance will not decrease so much.

That is, if the EHC 1 is abnormal, the temperature of the catalyst carrier 3 will not go up before the point in time TB at which the internal combustion engine 10 is started. For this reason, after the point in time TB at which the internal combustion engine 10 is started, a larger amount of condensed water will be generated than that before the point in time TB. Accordingly, the value of the insulation resistance will decrease to a large extent. Then, when the temperature of the electrodes 7 or the insulation parts 8 goes up due to the heat of the exhaust gas, the water attached or adhered to these will evaporate, so the value of the insulation resistance will become large.

In this embodiment, in a period of time in which the value of the insulation resistance decreases to a large extent in the case where the EHC 1 is abnormal, the value of the insulation resistance is detected and is compared with the threshold value R2. This threshold value R2 has been beforehand obtained through experiments or the like as an upper limit value of the insulation resistance value which is detected in the case where the EHC 1 is abnormal.

Here, note that what is compared with the threshold value R2 may be a minimum value of the insulation resistance value in the period of time from TC to TD, or may be an average value or a maximum value of the insulation resistance value in this period of time. In addition, it may be a value of the insulation resistance at an arbitrary point in time in the period of time from TC to TD.

Figure 4:
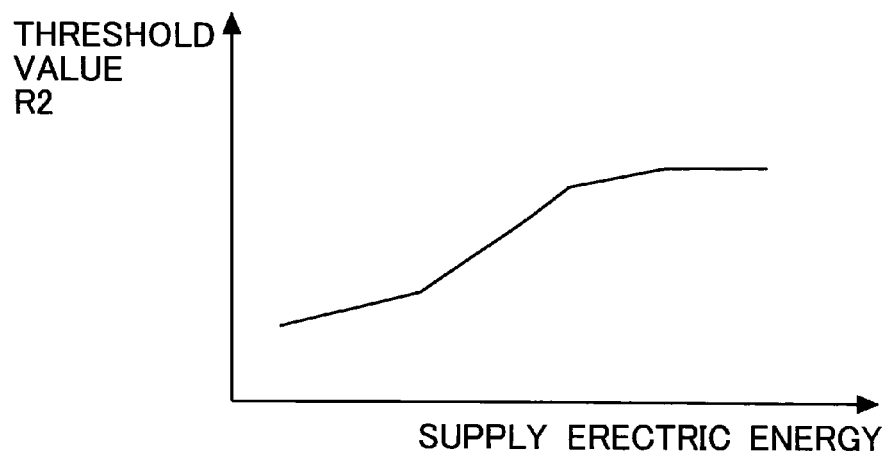
FIG. 4 is a view showing the relation between an electric energy to be supplied to a catalyst carrier and a threshold value.

In addition, the value of the insulation resistance at the time of the starting of the internal combustion engine 10 also changes with an electric energy supplied to the catalyst carrier 3. Here, FIG. 4 is a view showing the relation between the electric energy supplied to the catalyst carrier 3 and the threshold value R2 (the upper limit value of the insulation resistance value in the case where the EHC 1 is abnormal). Even if the EHC 1 is normal, when the electric energy supplied to the catalyst carrier 3 is small, there is a fear that condensed water may be generated. At this time, the lower the electric energy, the larger the amount of generation of the condensed water becomes. In addition, even if the EHC 1 has an abnormality, in cases where electricity flows through the catalyst carrier 3, the larger the electric energy, the higher the temperature of the catalyst carrier 3 becomes. Accordingly, the value of the insulation resistance becomes larger, too.

In this manner, it is necessary to distinguish whether the value of the insulation resistance is small because the EHC 1 has an abnormality, or whether the value of the insulation resistance is small because the electric energy supplied is small. In contrast to this, in this embodiment, the larger the electric energy supplied to the catalyst carrier 3, the larger the threshold value R2 is made, as shown in FIG. 4.

Figure 5:
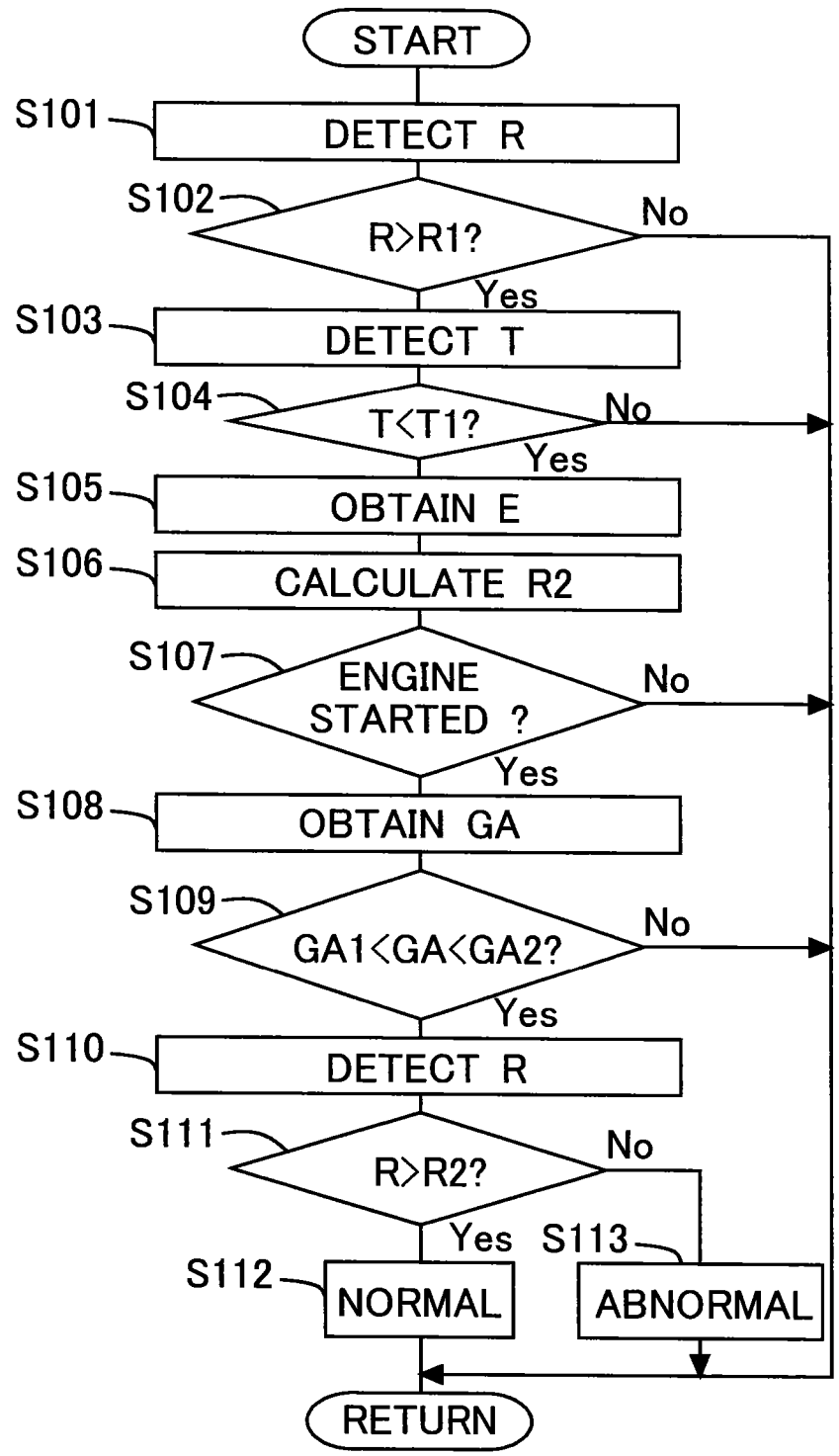
FIG. 5 is a flow chart showing a flow for determining an abnormality of an EHC according to a first embodiment.

Now, FIG. 5 is a flow chart showing a flow or routine for determining an abnormality of the EHC 1 according to a first embodiment. This routine is carried out by means of the ECU 20 at each predetermined time interval.

In step S101, a value R of the insulation resistance (hereinafter referred to as an insulation resistance value R) before the starting of the internal combustion engine 10 is detected. The value R of the insulation resistance is detected in a repeated manner until the starting of the internal combustion engine 10, and eventually, the value R of the insulation resistance at the point in time at which the starting of the internal combustion engine 10 is commenced is detected.

In step S102, it is determined whether the insulation resistance value R detected in step S101 is larger than a threshold value R1. The threshold value R1 referred to herein is an upper limit value of the insulation resistance value when water or PM has adhered to the mat 5 or the inner pipe 6, for example. Here, when water or the PM has adhered to the mat 5 or the inner pipe 6, electricity can flow to the case 4 from the catalyst carrier 3 through this water or PM. In such a case, even if the EHC 1 is normal, the insulation resistance value R measured by the measuring device 21 becomes small. Thus, in cases where the insulation resistance value R has already become low before the starting of the internal combustion engine 10, it becomes difficult to determine the abnormality of the EHC 1 in an accurate manner. Accordingly, an abnormality determination is carried out, only when the insulation resistance value R is high to a certain extent before the starting of the internal combustion engine 10.

Here, note that in this step, an amount of adhesion (deposition) of the water or the PM in the EHC 1 may be estimated, and it may be determined whether the amount of adhesion thereof is less than a threshold value. This threshold value is a lower limit value of the amount of adhesion with which accuracy in the abnormality determination of the EHC 1 becomes out of an allowable range.

Here, the amount of generation of condensed water is decided by an air fuel ratio, the temperature of the exhaust pipe 2 and the amount of intake air, at the time of the starting of the internal combustion engine 10. In addition, the higher the temperature of the exhaust pipe 2, the larger the amount of evaporation of the condensed water becomes. An amount of adhesion of the condensed water at a current point in time is calculated by integrating, based on these relations, the amount of generation and the amount of evaporation of the condensed water until the last operation of the internal combustion engine 10.

In addition, the amount of generation of the PM is decided by the temperature of the cooling water, the air fuel ratio and the amount of intake air, at the time of the starting of the internal combustion engine 10. Moreover, the PM is oxidized when the temperature thereof is high and when there is a large amount of oxygen, so there it is possible to calculate an amount of oxidation of the PM from the temperature of the exhaust gas and a period of time in which fuel cut-off has been carried out. An amount of adhesion of the PM at the current point in time is calculated by integrating, based on these relations, the amount of generation and the amount of oxidation of the PM until the last operation of the internal combustion engine 10.

Then, in cases where an affirmative determination is made in step S102, the routine goes to step S103. On the other hand, in cases where a negative determination is made in step S102, this routine is ended, without carrying out an abnormality determination.

In step S103, a temperature T of the cooling water before the starting of the internal combustion engine 10 is detected. The temperature of the cooling water is detected by the water temperature sensor 22. The temperature T of the cooling water is detected in a repeated manner until the starting of the internal combustion engine 10, and eventually, the temperature T of the cooling water at the point in time at which the starting of the internal combustion engine 10 is commenced is detected.

In step S104, it is determined whether the temperature T of the cooling water detected in step S103 is less than a threshold value T1. Here, in cases where the temperature of the cooling water is high, it is considered that the temperature of the exhaust pipe 2 or the EHC 1 is also high. In such a case, it becomes difficult for water (moisture) to condense. In that case, even if an abnormality has occurred in the EHC 1, water may not condense, there will be a fear that the value of the insulation resistance may not become low. Accordingly, an abnormality determination is carried out, only when the temperature of the cooling water in the internal combustion engine 10 is low to a certain extent. That is, the threshold value T1 can be set to a lower limit value of the temperature at which water does not condense in the electrodes 7 or the insulation part 8, for example. This threshold value T1 is 60 degrees C., for example.

In cases where an affirmative determination is made in step S104, the routine advances to step S105. On the other hand, in cases where a negative determination is made in step S104, this routine is ended, without carrying out an abnormality determination.

In step S105, the electric energy E to be supplied to the catalyst carrier 3 before the starting of the internal combustion engine 10 is obtained. As this electric energy E, there is used a value which is obtained through integration by the ECU 20.

Here, note that the supply of electric power to the catalyst carrier 3 is commenced at the time when it is expected that the internal combustion engine 10 is started up. For example, when a door of a vehicle was opened, or when undocking of a vehicle door was carried out from the outside of the vehicle, or when the driver of the vehicle sat on the driver's seat, or when a predetermined load was reached in a hybrid vehicle, or when an operation for starting the internal combustion engine 10 was carried out, etc., it can be expected that the internal combustion engine 10 will be started. In addition, the supply of electric power is ended at the point in time TB at which the starting of the internal combustion engine 10 is commenced.

In step S106, the threshold value R2 for the insulation resistance value is calculated based on the electric energy E obtained in step S105. This threshold value R2 is an upper limit value of the insulation resistance value R which is detected when the EHC 1 has an abnormality. This threshold value R2 is calculated based on the relation shown in FIG. 4. The relation shown in FIG. 4 has been obtained in advance through experiments, etc.

In step S107, it is determined whether the internal combustion engine 10 has been started. Due to the starting of the internal combustion engine 10, the supply of electric power to the catalyst carrier 3 is stopped.

In step S108, an amount of intake air GA which has been integrated after the starting of the internal combustion engine 10 is obtained. This amount of intake air GA is a sum total of the amount of air which has been sucked into the internal combustion engine after the internal combustion engine 10 is started, and is obtained by integrating the amount of intake air detected by the air flow meter 12. This amount of intake air GA has a correlation with the time at which condensed water is generated when the EHC 1 has an abnormality, so the time to detect the insulation resistance value R is decided based on the amount of intake air GA.

In step S109, it is determined whether the amount of intake air GA obtained in step S108 is larger than a lower limit threshold value GA1, and smaller than an upper limit threshold value GA2. The lower limit threshold value GA1 corresponds to an amount of intake air at a point in time TC in FIG. 3. Also, the upper limit threshold value GA2 corresponds to an amount of intake air at a point in time TD in FIG. 3. The lower limit threshold value GA1 and the upper limit threshold value GA2 can be obtained in advance through experiments, etc. In cases where the EHC 1 has an abnormality, when the amount of intake air GA is larger than the lower limit threshold value GA1 and smaller than the upper limit threshold value GA2, the insulation resistance value R becomes the smallest. Accordingly, by carrying out an abnormality determination based on the insulation resistance value R in this period of time, it becomes possible to make a more accurate determination.

In cases where an affirmative determination is made in step S109, the routine advances to step S110, whereas in cases where a negative determination is made, this routine is ended.

In step S110, the insulation resistance value R is detected.

In step S111, it is determined whether the insulation resistance value R detected in step S110 is larger than the threshold value R2 calculated in step S106. Here, when the EHC 1 has an abnormality, the insulation resistance value R becomes equal to or less than the threshold value R2.

In cases where an affirmative determination is made in step S111, the routine advances to step S112, in which a determination is made that the EHC 1 is normal. On the other hand, in cases where a negative determination is made in step S111, the routine advances to step S113, in which a determination is made that the EHC 1 is abnormal. Here, note that in this embodiment, the ECU 20, which carries out the processing of steps S111, S113 corresponds to a determination unit in the present invention.

As described above, according to this embodiment, a determination as to whether the EHC 1 is normal can be made, by carrying out electrical energization to the EHC 1 before the starting of the internal combustion engine 10, and making a comparison of the insulation resistance value R, which is detected in the predetermined period of time after the starting of the internal combustion engine 10, with the threshold value R2.

Second Embodiment

In this second embodiment, the above-mentioned threshold value R2 is changed according to the electric energy E supplied to the catalyst carrier 3 before the starting of the internal combustion engine 10, and the temperature T of the cooling water at the time of the starting of the internal combustion engine 10. The other devices, parts and so on are the same as those in the above-mentioned first embodiment, so the explanation thereof is omitted.

Here, with respect to the electric energy E supplied to the catalyst carrier 3 before the starting of the internal combustion engine 10, a plurality of modes can be considered according to a driver's request, an environmental condition, and so on. Then, the temperature of the catalyst carrier 3 at the time of the starting of the internal combustion engine 10 is influenced by this electric energy E. For this reason, the value of the insulation resistance after the starting of the internal combustion engine 10 is also affected by the influence of the electric energy E.

In addition, the amount of condensed water generated in the electrodes 7 or the insulation parts 8 is changed according to the temperature T of the cooling water in the internal combustion engine 10 at the time of the starting of the internal combustion engine 10. For this reason, the value of the insulation resistance after the starting of the internal combustion engine 10 is also affected by the influence of the temperature T of the cooling water.

Figure 6:
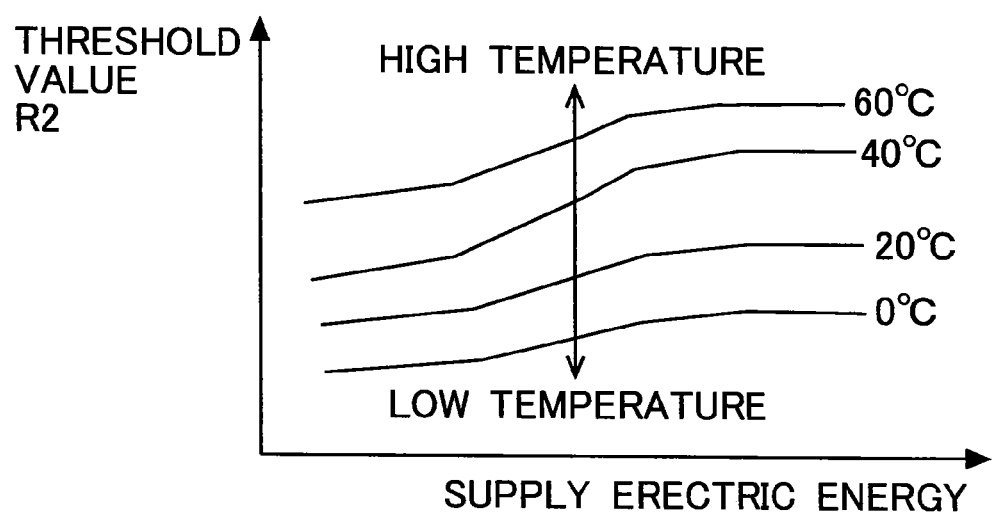
FIG. 6 is a view showing the relation between an electric energy to be supplied to a catalyst carrier and a threshold value.

In this second embodiment, the threshold value R2 is corrected according to the electric energy E supplied to the catalyst carrier 3 before the starting of the internal combustion engine 10, and the temperature T of the cooling water at the time of the starting of the internal combustion engine 10. FIG. 6 is a view showing the relation between the electric energy to be supplied to the catalyst carrier 3 and the threshold value R2. The larger the electric energy E to be supplied to the catalyst carrier 3, the larger the threshold value R2 is made. Also, the higher the temperature T of the cooling water, the larger the threshold value R2 is made. These relations can be obtained in advance through experiments, etc.

Figure 7:
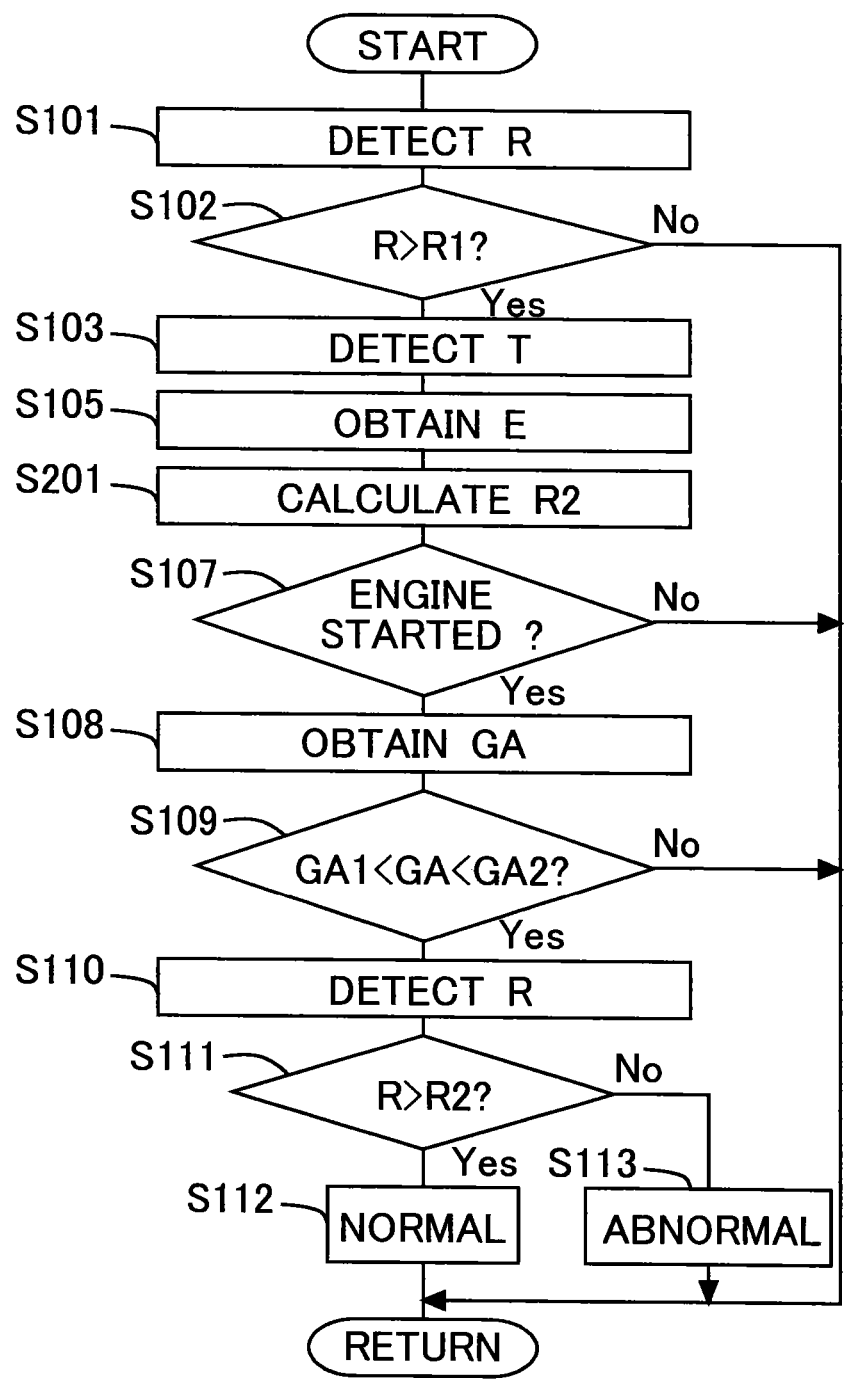
FIG. 7 is a flow chart showing a flow for determining an abnormality of an EHC according to a second embodiment.

FIG. 7 is a flow chart showing a flow or routine for determining an abnormality of the EHC 1 according to the second embodiment. This routine is carried out by means of the ECU 20 at each predetermined time interval. Here, note that for those steps in which the same processing as in the above-mentioned flow is carried out, the same symbols are attached and an explanation thereof is omitted.

In this routine, processing goes to step S201 after step S105. Then, in step S201, the threshold value R2 is calculated from the relation shown in FIG. 6 based on the temperature T of the cooling water detected in step S103 and the electric energy E obtained in step S105. The relation shown in FIG. 6 has been obtained beforehand through experiments, etc., and stored in the ECU 20. After that, the routine advances to step S107. Here, note that in this embodiment, the ECU 20, which carries out the processing of steps S111, S113 and S201 corresponds to a determination unit in the present invention.

In this manner, the abnormality of the EHC 1 is determined in consideration of the electric energy E supplied to the catalyst carrier 3 before the starting of the internal combustion engine 10, and the temperature T of the cooling water at the time of the starting of the internal combustion engine 10, thus making it possible to make a more accurate determination. In addition, even if modes of the supply of electric power are different, they can be dealt with.

Third Embodiment

In this third embodiment, the above-mentioned threshold value R2 is changed based on the value of the insulation resistance at the time of the starting of the internal combustion engine 10 or at the start of the supply of electric power to the catalyst carrier 3. Here, note that the above-mentioned threshold value R2 may be changed based on the value of the insulation resistance before the starting of the internal combustion engine 10. The other devices, parts and so on are the same as those in the above-mentioned embodiments, so the explanation thereof is omitted.

Here, when PM or water has adhered to the mat 5 or the inner pipe 6, electricity may flow between the catalyst carrier 3 and the case 4 through the PM or water. Then, the value of the insulation resistance measured by the measuring device 21 becomes low due to the PM or water. That is, even before the starting of the internal combustion engine 10, the value of the insulation resistance may become low due to the PM or water which has already adhered to the EHC 1.

Accordingly, in this embodiment, in cases where the value of the insulation resistance has already become low before the starting of the internal combustion engine 10, the threshold value R2 is corrected according to this value of the insulation resistance. For example, the threshold value R2 is corrected based on the value of the insulation resistance at the time of the starting of the internal combustion engine 10 or at the start of the supply of electric power to the catalyst carrier 3.

Figure 8:
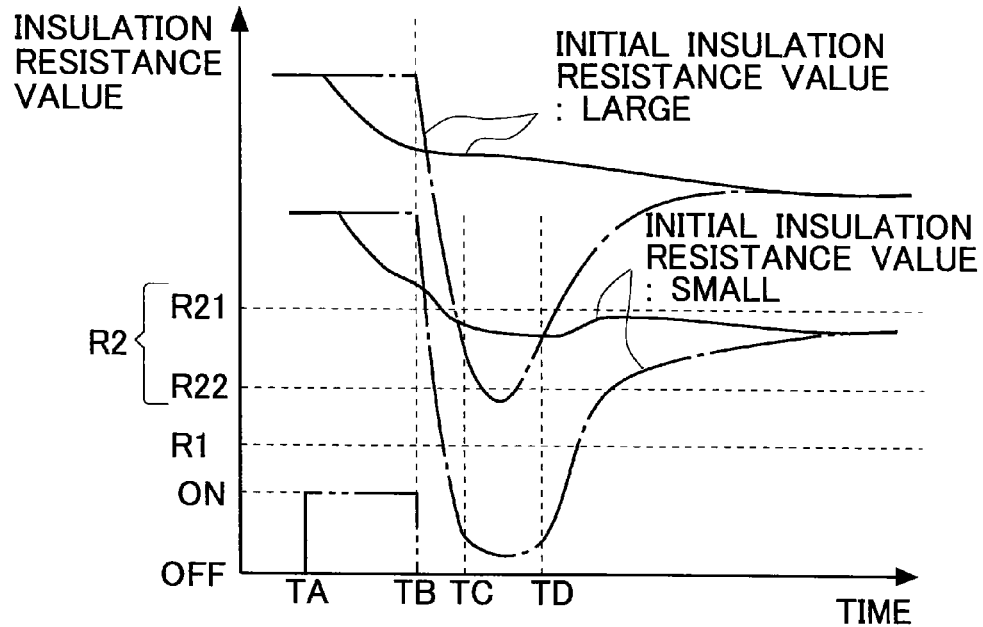
FIG. 8 is a time chart showing the change over time of a value of an insulation resistance before and after starting of an internal combustion engine.

Here, FIG. 8 is a time chart showing the change over time of the value of the insulation resistance before and after the starting of the internal combustion engine 10. A solid line indicates the value of the insulation resistance at the time of normal operation, and an alternate long and short dash line indicates the value of the insulation resistance at the time of abnormal operation. In addition, an alternate long and two short dashes line indicates supply power. When the supply power is on, electric power is supplied to the catalyst carrier 3, whereas when the supply power is off, the supply of electric power to the catalyst carrier 3 is stopped. In FIG. 8, "initial insulation resistance value: large" represents a case where the insulation resistance value at the time of the starting of the internal combustion engine 10 or at the start of the supply of electric power to the catalyst carrier 3 is relatively large, whereas "initial insulation resistance value: small" represents a case where the insulation resistance value at the time of the starting of the internal combustion engine 10 or at the start of the supply of electric power to the catalyst carrier 3 is relatively small.

Here, note that in FIG. 8, R21 is a threshold value in the case when the initial value of the insulation resistance is relatively large, and R22 is a threshold value in the case when the initial value of the insulation resistance is relatively small. In addition, R1 is a threshold value with which the insulation resistance value R is compared in the above-mentioned step S102, and is an upper limit value of the insulation resistance value when water or PM has adhered to the EHC 1.

When PM or the like has adhered to the mat 5 or the like before the starting of the internal combustion engine 10, the insulation resistance value at the time of the starting of the internal combustion engine 10 or at the start of the supply of electric power to the catalyst carrier 3 becomes relatively small, as shown in FIG. 8. On the other hand, when there is no adhesion of PM, etc., the insulation resistance value at the time of the starting of the internal combustion engine 10 or at the start of the supply of electric power to the catalyst carrier 3 becomes relatively large.

Here, for example, when the threshold value R21, which is set in the case where the initial value of the insulation resistance is relatively large, is also applied to a case where the initial value of the insulation resistance is relatively small, even if the EHC 1 is normal, there will be a fear that the insulation resistance value R may become equal to or less than the threshold value R21. On the other hand, when the threshold value R22, which is set in the case where the initial value of the insulation resistance is relatively small, is also applied to a case where the initial value of the insulation resistance is relatively large, even if the EHC 1 is abnormal, there will be a fear that the insulation resistance value R can become larger than the threshold value R22. In this manner, when the threshold value is kept as a constant value, there will be a fear that the accuracy of the abnormality determination may decrease.

In contrast to this, when the threshold value is collected according to the initial value of the insulation resistance, it will become possible to make a more accurate abnormality determination.

Figure 9:
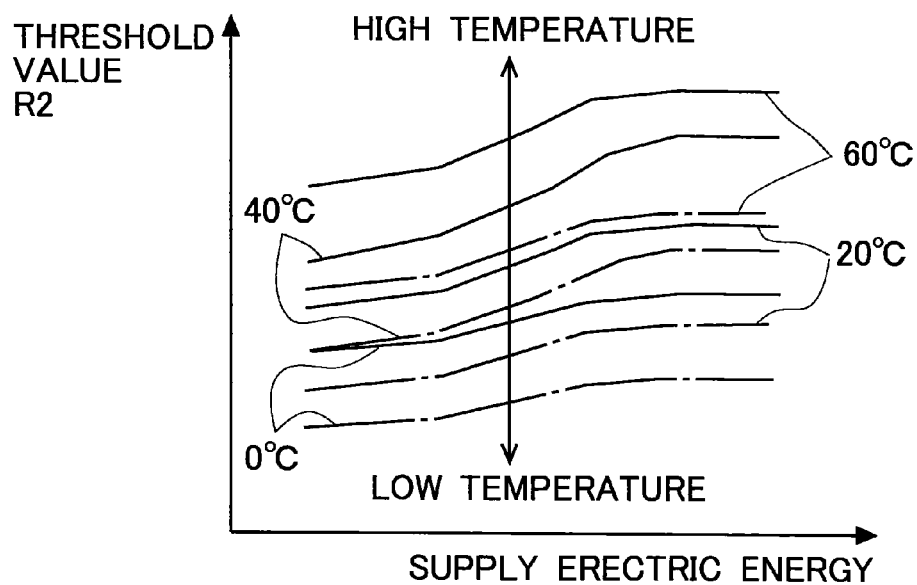
FIG. 9 is a view showing the relation between an electric energy to be supplied to a catalyst carrier and a threshold value.

Here, FIG. 9 is a view showing the relation between the electric energy to be supplied to the catalyst carrier 3 and the threshold value R2. A solid line represents a case where the initial value of the insulation resistance is relatively large, and an alternate long and short dash line represents a case where the initial value of the insulation resistance is relatively small. In addition, the temperature described in FIG. 9 represents the temperature T of the cooling water. Then, the higher the value of the insulation resistance, the larger the threshold value R2 is made. Also, the larger the electric energy to be supplied to the catalyst carrier 3, the larger the threshold value R2 is made. Further, the higher the temperature T of the cooling water, the larger the threshold value R2 is made. These relations can be obtained in advance through experiments, etc. Here, note that in this embodiment, the threshold value is set for two cases, respectively, i.e., one case where the initial value of the insulation resistance is large, and the other case where the initial value of the insulation resistance is small, but the threshold value may be set for three or more cases, or the threshold value may be set in a stepless manner.

Figure 10:
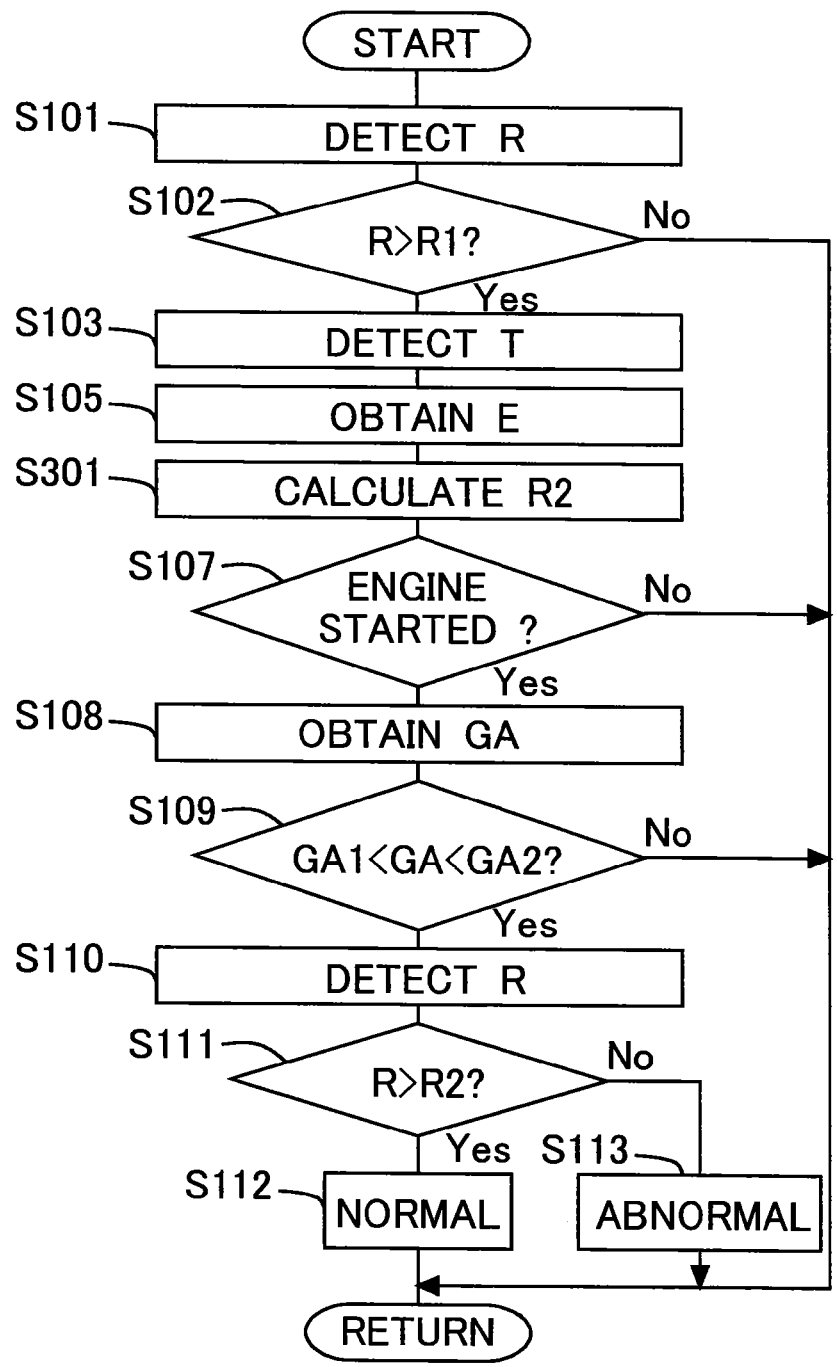
FIG. 10 is a flow chart showing a flow for determining an abnormality of an EHC according to a third embodiment.

FIG. 10 is a flow chart showing a flow or routine for determining an abnormality of the EHC 1 according to the third embodiment. This routine is carried out by means of the ECU 20 at each predetermined time interval. Here, note that for those steps in which the same processing as in the above-mentioned flow is carried out, the same symbols are attached and an explanation thereof is omitted. Also, note that in step S101, the value of the insulation resistance can be detected at the time of the start of the supply of electric power to the catalyst carrier 3.

In this routine, processing goes to step S301 after step S105. Then, in step S301, the threshold value R2 is calculated from the relation shown in FIG. 9 based on the insulation resistance value R detected in step S101, the temperature T of the cooling water detected in step S103, and the electric energy E obtained in step S105. Here, note that the relation shown in FIG. 9 has been obtained beforehand through experiments, etc., and stored in the ECU 20. After that, the routine advances to step S108. Here, note that in this embodiment, the ECU 20, which carries out the processing of steps S111, S113 and S301 corresponds to a determination unit in the present invention.

In this manner, the abnormality of the EHC 1 is determined in consideration of the insulation resistance at the time of the starting of the internal combustion engine 10 or at the start of the supply of electric power to the catalyst carrier 3, the electric energy E supplied to the catalyst carrier 3 before the starting of the internal combustion engine 10, and the temperature T of the cooling water at the time of the starting of the internal combustion engine 10, thus making it possible to make a more accurate determination.

Fourth Embodiment

In this fourth embodiment, electric power is supplied to the catalyst carrier 3 after the starting of the internal combustion engine 10, too. According to this, although the temperature of the catalyst carrier 3 does not rise to a sufficient extent before the starting of the internal combustion engine 10, the temperature thereof can be made to rise in a quick manner after the starting of the internal combustion engine 10. The other devices, parts and so on are the same as those in the above-mentioned embodiments, so the explanation thereof is omitted.

Here, even if electric power is supplied to the catalyst carrier 3 from before the starting of the internal combustion engine 10, in cases where a period of time until the starting of the internal combustion engine 10 is short, the electric energy E, which will be supplied by the time the internal combustion engine 10 is started, becomes relatively small. In that case, even if the EHC 1 is normal, it becomes easy for condensed water to be generated after the starting of the internal combustion engine 10, and there is a fear that the value of the insulation resistance may decrease. On the other hand, by supplying electric power to the catalyst carrier 3 after the starting of the internal combustion engine 10, the value of the insulation resistance can be restored in a quick manner. Then, when the EHC 1 is normal, the value of the insulation resistance is detected at the time in which the value of the insulation resistance has been restored, so that when the value of the insulation resistance is large, a determination can be made that the EHC 1 is normal. On the other hand, when the value of the insulation resistance is small at this time, a determination can be made that there is an abnormality in the EHC 1.

Figure 11:
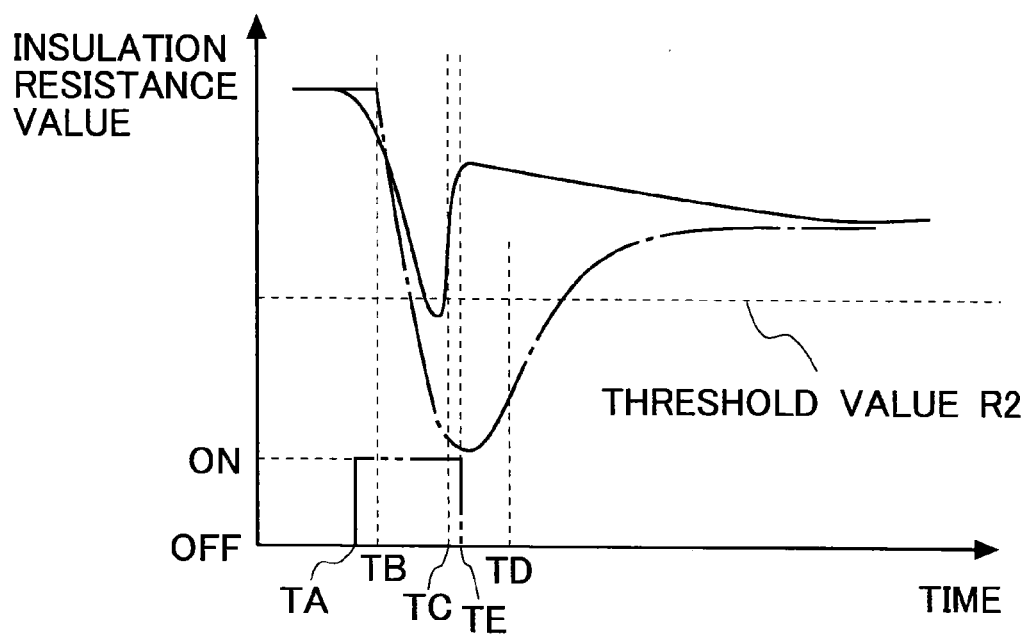
FIG. 11 is a time chart showing the change over time of a value of an insulation resistance before and after starting of an internal combustion engine.

Here, FIG. 11 is a time chart showing the change over time of the value of the insulation resistance before and after the starting of the internal combustion engine 10. A solid line indicates the value of the insulation resistance at the time of normal operation, and an alternate long and short dash line indicates the value of the insulation resistance at the time of abnormal operation. In addition, an alternate long and two short dashes line indicates supply power. When the supply power is on, electric power is supplied to the catalyst carrier 3, whereas when the supply power is off, the supply of electric power to the catalyst carrier 3 is stopped.

At a point in time indicated by TA, the supply of electric power to the catalyst carrier 3 is started. At a point in time indicated by TB, the internal combustion engine 10 is started up. At the point in time TB at which the internal combustion engine 10 is started, the supply of electric power to the catalyst carrier 3 is carried out in a continuous manner, and the supply of electric power is performed until a point in time indicated by TE.

Then, in this embodiment, based on the value of the insulation resistance in a period of time from TC to TD, it is determined whether the EHC 1 is abnormal. The period of time from TC to TD has been obtained in advance through experiments, etc., as a period of time in which the value of the insulation resistance is restored in cases where sufficient electric power is supplied to the catalyst carrier 3, whereas the value of the insulation resistance is not restored in cases where sufficient electric power is not supplied to the catalyst carrier 3. Here, note that, in this embodiment, the period of time from TC to TD is defined in association with an integrated value of an amount of intake air in the internal combustion engine 10. That is, an amount of condensed water generated in the electrode chambers 9 changes according to the integrated value of the amount of intake air in the internal combustion engine 10, and hence, a period of time in which the amount of condensed water is large is defined based on the integrated value of the amount of intake air.

Here, if the temperature of the catalyst carrier 3 is not high enough by the time the internal combustion engine 10 is started even if the EHC 1 is normal, condensed water is generated from the point in time TB at which the internal combustion engine 10 is started, and the value of the insulation resistance decreases. If the EHC 1 is normal, condensed water will be evaporated quickly by supplying electric power to the catalyst carrier 3 after that, too, the value of the insulation resistance is also restored quickly. For this reason, in the period of time from TC to TD, the value of the insulation resistance becomes larger than the threshold value R2.

On the other hand, when the EHC 1 is abnormal, from the point in time TB at which the internal combustion engine 10 is started, the value of the insulation resistance will decrease to a large extent. Then, after the starting of the internal combustion engine 10, electric power is not supplied in actuality even if intended to be supplied, so condensed water does not evaporate until the temperature of the catalyst carrier 3 is raised high due to the heat of the exhaust gas. As a result, when the EHC 1 is abnormal, the value of the insulation resistance during the period of time from TC to TD becomes equal to or less than the threshold value R2.

That is, if the EHC 1 is normal, condensed water evaporates quickly even if generated after the point in time TB at which the internal combustion engine 10 is started. Accordingly, the value of the insulation resistance becomes large in a quick manner. On the other hand, if the EHC 1 is abnormal, a larger amount of condensed water will be generated after the point in time TB at which the internal combustion engine 10 is started than before that point in time. Accordingly, the value of the insulation resistance will decrease to a large extent. Then, it takes time until the temperature of the electrodes 7 or the insulation parts 8 goes up due to the heat of the exhaust gas, so it also takes time until the value of the insulation resistance will become large.

In this embodiment, in the period of time (i.e., in the period of time from TC to TD) in which in the case where the EHC 1 is normal, the value of the insulation resistance has been restored, and in the case where the EHC 1 is abnormal, the value of the insulation resistance has not been restored, the value of the insulation resistance is detected, and is compared with the threshold value R2. This threshold value R2 has been beforehand obtained through experiments or the like as an upper limit value of the insulation resistance value which is detected in the case where the EHC 1 is abnormal.

Here, note that what is compared with the threshold value R2 may be a minimum value of the insulation resistance value in the period of time from TC to TD, or may be an average value or a maximum value of the insulation resistance value in this period of time. In addition, it may be a value of the insulation resistance at an arbitrary point in time in the period of time from TC to TD.

Figure 12:
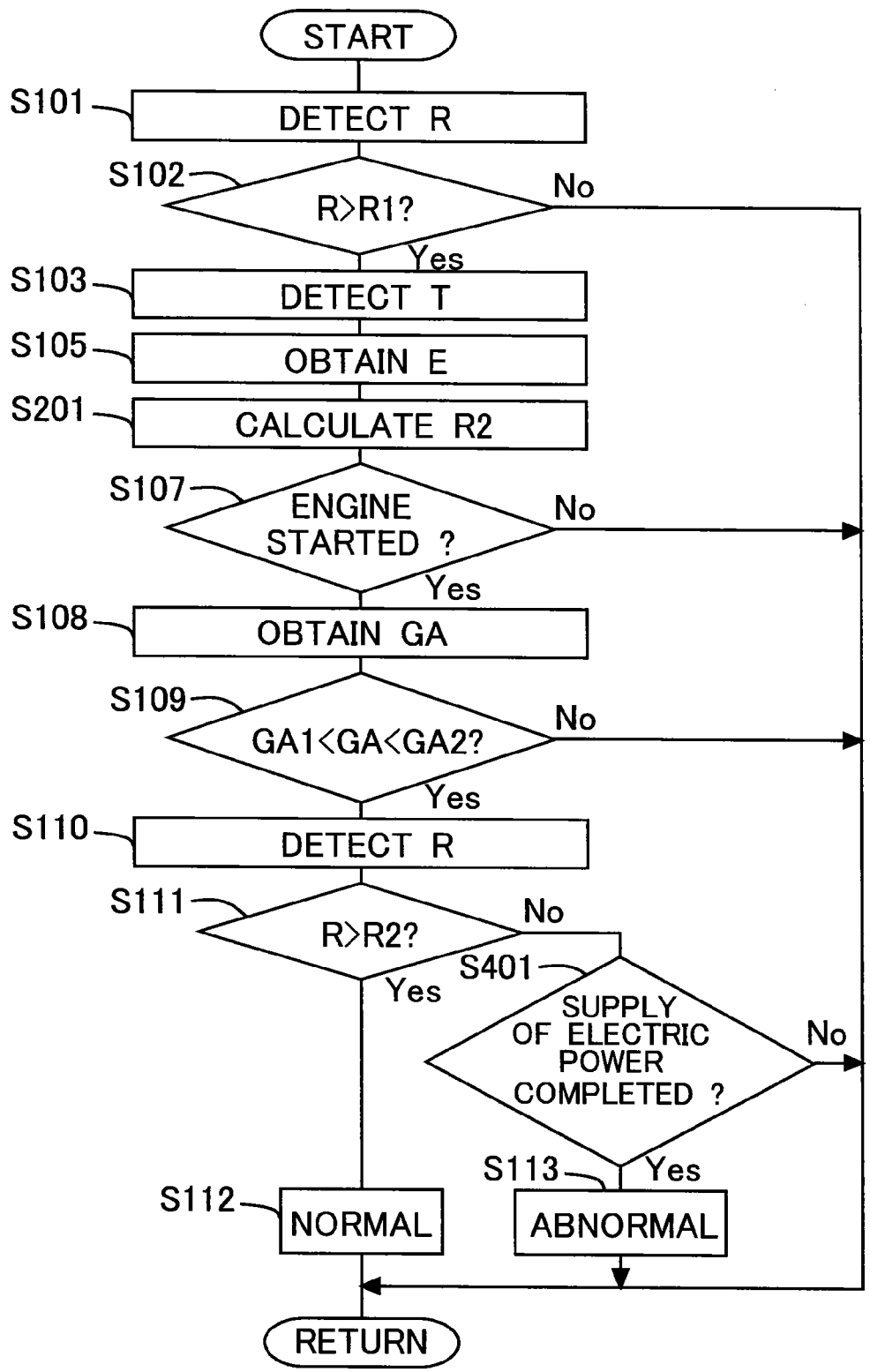
FIG. 12 is a flow chart showing a flow for determining an abnormality of an EHC according to a fourth embodiment.

FIG. 12 is a flow chart showing a flow or routine for determining an abnormality of the EHC 1 according to the fourth embodiment. This routine is carried out by means of the ECU 20 at each predetermined time interval. Here, note that for those steps in which the same processing as in the above-mentioned flow is carried out, the same symbols are attached and an explanation thereof is omitted.

In this routine, in cases where a negative determination is made in step S111, the processing advances to step S401. In step S401, it is determined whether the supply of electric power to the catalyst carrier 3 has been completed. For example, when the electric energy E set in advance is reached, a determination is made that the supply of electric power has been completed, whereby the supply of electric power is stopped. Also, when electric power has been supplied for a predetermined period of time, a determination may be made that the supply of electric power has been completed, and the supply of electric power may be stopped.

Then, in cases where an affirmative determination is made in step S401, the value of the insulation resistance should have been recovered if the EHC 1 is normal, but in spite of this, the value of the insulation resistance has not been restored, so the routine advances to step S113. On the other hand, in cases where a negative determination is made in step S401, the value of the insulation resistance has not been restored even if the EHC 1 is normal, and hence, an abnormality determination can not be made, and this routine is ended. Here, note that in this embodiment, the ECU 20, which carries out the processing of steps S111, S113, S201 and S401 corresponds to a determination unit in the present invention.

In this manner, by determining the abnormality of the EHC 1 based on the value of the insulation resistance at the time when electric power is supplied to the catalyst carrier 3 after the starting of the internal combustion engine 10, it becomes possible to make a more accurate determination.

EXPLANATION OF REFERENCE NUMERALS AND CHARACTERS 1 electrically heated catalyst (EHC)
2 exhaust pipe
3 catalyst carrier
4 case
5 mat
6 inner pipe 7 electrodes
8 insulation parts
9 electrode chambers
10 internal combustion engine
11 intake pipe
12 air flow meter
13 catalyst
14 throttle valve
20 ECU
21 measuring device
22 water temperature sensor
25 power control unit
26 battery

The invention claimed is:

1. A abnormality detection apparatus for an electrically heated catalyst comprising:
    a heat generation element that is arranged in an exhaust passage of an internal combustion engine, and generates heat by electrical energization thereof; and
    an insulation part that provides electrical insulation so as to prevent electricity from flowing through said exhaust passage when said heat generation element is electrically energized;
    wherein provision is made for a determination unit which makes a determination that abnormality has occurred in said electrically heating catalyst, in cases where said heat generation element is electrically energized from before starting of said internal combustion engine, and in cases where a value of an insulation resistance of said insulation part after a predetermined period of time has elapsed from the starting of said internal combustion engine is equal to or less than a threshold value.

2. The abnormality detection apparatus for an electrically heated catalyst as set forth in claim 1, wherein
    said determination unit makes said threshold value larger in accordance with the increasing temperature of said internal combustion engine at the time of the starting of said internal combustion engine.

3. The abnormality detection apparatus for an electrically heated catalyst as set forth in claim 1, wherein
    said determination unit makes said threshold value larger in accordance with the increasing value of said insulation resistance at the time of the starting of said internal combustion engine.

4. The abnormality detection apparatus for an electrically heated catalyst as set forth in claim 1, wherein
    said determination unit makes said threshold value larger in accordance with the increasing electric energy which has been supplied to said heat generation element by the time said internal combustion engine is started.

5. The abnormality detection apparatus for an electrically heated catalyst as set forth in claim 1, wherein
    said determination unit makes a determination that abnormality has occurred in said electrically heating catalyst, in cases where said heat generation element is electrically energized from before the starting of said internal combustion engine until after the starting of said internal combustion engine, and in cases where the value of the insulation resistance of said insulation part after the predetermined period of time has elapsed from the starting of said internal combustion engine is equal to or less than a threshold value.

* * * * *